United States Patent [19]

Cymbalisty et al.

[11] 4,372,174

[45] Feb. 8, 1983

[54] METHOD AND APPARATUS FOR SAMPLING A CORE OF TAR SAND

[75] Inventors: Lubomyr M. Cymbalisty; Alvin J. Maskwa; Lloyd W. Trevoy; Jan Wojno, all of Edmonton, Canada

[73] Assignees: Petro-Canada Exploration Inc., Calgary; Her Majesty the Queen in right of the Province of Alberta, Government of the Province of Alberta, Department of Energy and Natural Resources, Alberta Syncrude Equity, Edmonton; PanCanadian Petroleum Limited, Calgary; Esso Resources Canada Ltd., Calgary; Canada-Cities Service, Ltd., Calgary; Gulf Canada Limited, Calgary; Alberta Energy Company Ltd., Calgary; Hudson's Bay Oil and Gas Company Limited, Calgary; Petrofina Canada Inc., Calgary, all of Canada

[21] Appl. No.: 260,365

[22] Filed: May 4, 1981

[51] Int. Cl.³ .............................................. G01N 1/04
[52] U.S. Cl. .............................. 73/863.11; 73/864.41; 83/170; 83/471.2; 83/877
[58] Field of Search ...................... 73/863.11, 864.41; 83/471, 471.2, 471.3, 876, 877, 878, 170

[56] References Cited

U.S. PATENT DOCUMENTS

| 61,912 | 2/1867 | Yaman | 83/877 |
| 2,216,989 | 10/1940 | St. Clair | 73/864.41 |
| 3,690,356 | 9/1972 | Holan | 83/877 |
| 3,900,975 | 8/1975 | Lightstone | 83/170 |
| 3,902,390 | 9/1975 | Darbo | 83/170 |

FOREIGN PATENT DOCUMENTS

626381 9/1978 U.S.S.R. ........................ 73/864.41

*Primary Examiner*—S. Clement Swisher

[57] ABSTRACT

The invention provides a method and apparatus for sampling a frozen core of tar sand. The frozen core is first cut transversely along its length to form a pair of slabs of semi-circular cross-section. A longitudinal sample portion of substantially triangular cross-section is then cut from the central portion of the still frozen slab. The triangular sample portion is ground in a cryogenic grinder to produce a finely divided, substantially homogeneous material from which small representative sub-samples may be obtained. The triangular sample portion is cut from the slab by a pair of angularly disposed circular saws carried along the length of the slab. The slab is supported and held by cradle means which fix the flat face of the slab in a predetermined plane. The longitudinal sample portion thus formed has a triangular cross-section of substantially constant cross-sectional area.

3 Claims, 11 Drawing Figures

METHOD AND APPARATUS FOR SAMPLING A CORE OF TAR SAND

FIELD OF THE INVENTION

This invention relates to a method and apparatus for sampling a frozen core of tar sand.

BACKGROUND OF THE INVENTION

The invention has been developed in connection with the operation of a mining-extraction plant for recovering bitumen from the Athabasca tar sands. In such an undertaking, it is necessary to have accurate information as to the composition of the material being mined and processed.

Before the section of the tar sand deposit to be exploited is actually mined, it is usual to drill and recover cores at spaced intervals. Each such cylindrical core of unconsolidated material is recovered from the core barrel in a closed plastic tube. The enclosed core is immediately frozen and stored under sub-zero temperature conditions.

To analyze the cylindrical core, only the inner portion of the core can be used. The mud used during drilling tends to penetrate and therefore contaminate the outer layers of the core.

Heretofore, when the core was to be examined, it would be cut transversely to form two slabs of semi-circular cross-section. One such slab would be examined visually. The other slab would be unfrozen and samples would be spooned out of its central portion at points along its length. These samples would then be analyzed.

A shortcoming of this technique is that the core composition varies along its length and thus the 'spot' samples are not as precisely representative as is desirable.

SUMMARY OF THE INVENTION

In accordance with the invention, a frozen, cylindrical core is cut transversely along its length to produce a pair of slabs of generally semi-circular cross-section. A longitudinal sample portion, having a substantially triangular cross-section of substantially constant area, is then cut from the comparatively uncontaminated central portion of a slab (which is still frozen). The still-frozen triangular sample portion is then ground and mixed in a cryogenic grinder to produce a substantially homogeneous and representative material. This material may then be sub-sampled to provide small samples suitable for analysis.

We use three machines to perform these steps. The first cuts the core transversely into slabs. The second cuts the longitudinal sample portion. And the third grinds and mixes the sample portion under cryogenic conditions to yield the homogeneous, representative sample.

The invention thus involves two concepts in combination. First, the tar sand is worked with while it is frozen. As a result, there is little opportunity for the bitumen component to exhibit its adhesiveness and cling to the machinery surfaces, thereby affecting the accuracy of the analysis. Secondly, the sample is representative of the full length of the core.

Broadly stated, in an apparatus aspect, the invention comprises a sampling apparatus for cutting a longitudinal sample portion from a substantially semi-circular slab of frozen tar sand core comprising: frame means; cradle means carried by the frame means for supporting and holding the slab in position for cutting with its flat face fixed in a pre-determined plane; carriage support means carried by the frame means and extending substantially parallel to said plane along said slab; saw carriage means mounted on the support means for movement therealong; a pair of angularly disposed, driven circular saws carried by the carriage means and operative to make nonintersecting cuts into the central portion of the slab to form a longitudinal sample portion having a generally triangular cross-section of substantially constant cross-sectional area, said sample portion having an apex still attached to the main body of the slab; whereby a sample portion may be produced which can easily be broken away from the slab and recovered.

In another broad aspect, the invention provides a method for sampling a frozen core of tar sand. The method comprises: cutting the core transversely to form a pair of slabs, each having a flat face and a curved face; sawing a pair of angularly directed cuts into the central portion of such a slab along at least part of its length to form a longitudinal sample portion having a generally triangular cross-section of substantially constant area; recovering the sample portion; and grinding at least part of the still frozen sample portion to form a generally homogeneous sample.

DESCRIPTION OF THE PREFERRED EMBODIMENT

Slabbing Saw Machine

Figure 1:
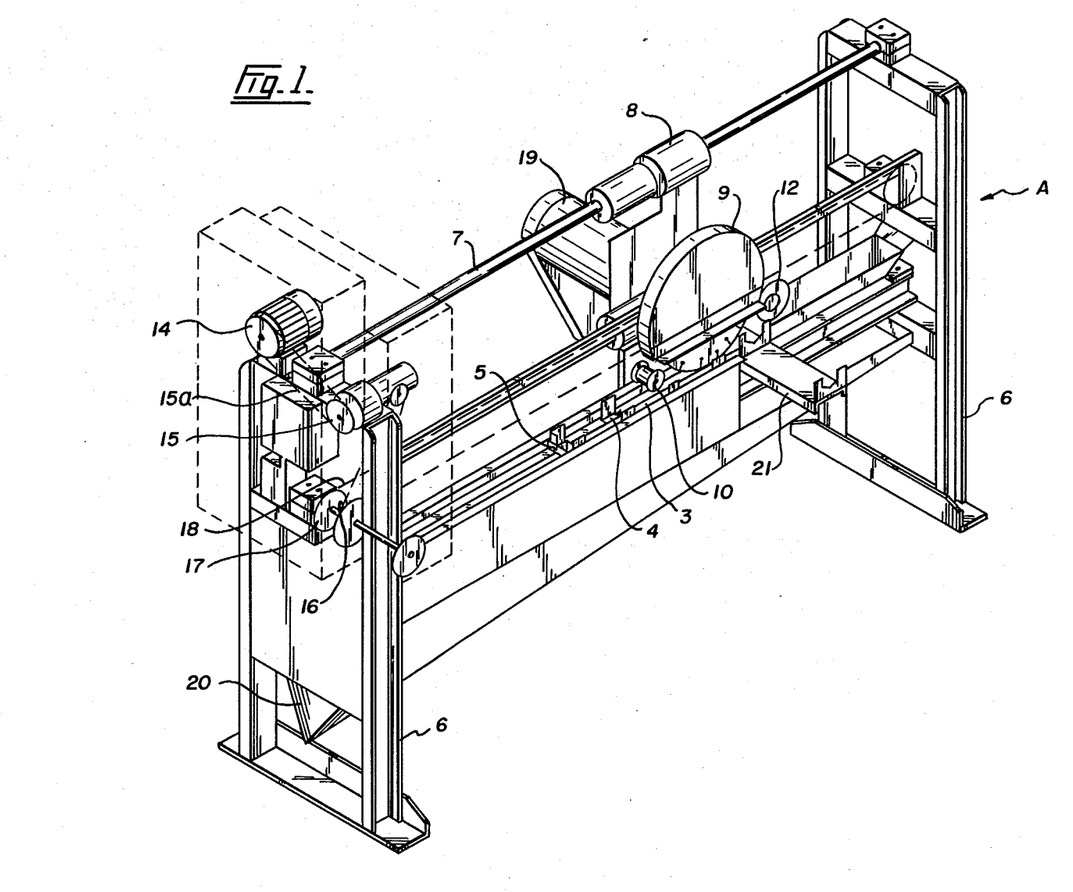
FIG. 1 is a perspective view of the slabbing saw machine for transversely cutting a cylindrical core of tar sand to form a pair of slabs.
Figure 2:
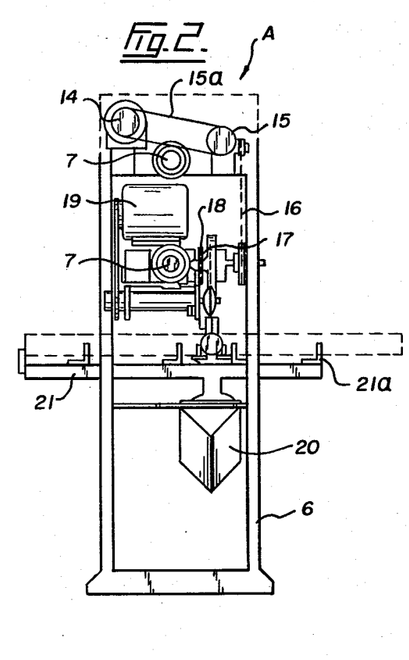
FIG. 2 is an end view of the slabbing saw machine.
Figure 3:
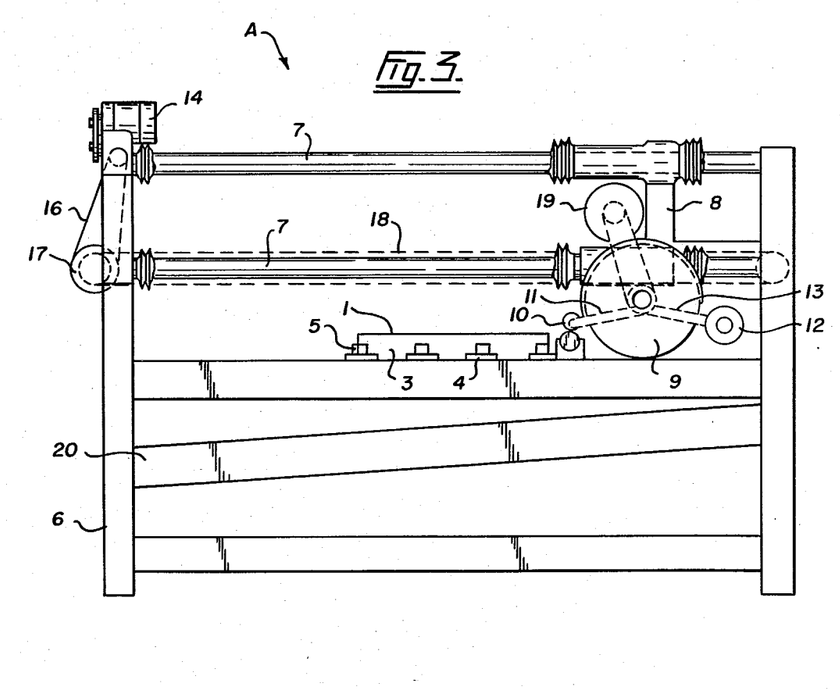
FIG. 3 is a side view of the slabbing saw machine.

The slabbing saw machine A is shown in FIGS. 1 to 3. This machine functions to cut the frozen tar sand core 1 transversely to form a pair of slabs 2.

The machine A includes a stationary cradle means 3 for supporting and holding the tar sand core 1 during the cutting operation. The cradle means 3 preferably comprises a plurality of spaced, concave-shaped brackets 4 which support the core, and stop means 5 at the forward end of the cradle means 3, against which the core 1 abuts. The stop means 5 prevents longitudinal movements of the core 1 during the cutting operation.

Frame means 6 are provided to support the cradle means 3 and other components of the machine A. The frame means 6 carry carriage support means, which extend parallel to the tar sand core 1 supported in the cradle means 3. The carriage support means comprises a pair of support rails 7.

Saw carriage means 8 are mounted on the rails 7 for movement therealong. A vertically disposed, circular saw 9 is carried by the saw carriage means 8. The saw 9 is operative to longitudinally cut the core 1, held in the cradle means 3, to form a pair of semi-circular slabs 2 as the saw carriage means 8 is moved along the support rails 7.

To facilitate the sawing operation, a core holddown means is included which is operative to hold the core 1 down in the cradle means 3 during sawing. A preferred form of the holddown means is a bobbin 10 attached by a spring-loaded extension arm 11 to the saw carriage means 8. The bobbin 10 has a concave surface which conforms with the surface of the core 1 being split. The bobbin is adapted to roll along the core and hold it in place during sawing.

The pair of slabs 2 produced have a tendency to adhere to each other or to re-freeze back together. To minimize this tendency, core splitting means are provided, which means are operative to hold the pair of slabs 2 apart during the cutting operation. Such splitting means may comprise a rotatable, wedge-like wheel 12 attached to the saw carriage means 8 by an extension arm 13 fitted with a downwardly operating spring (not shown). The spring is selected to provide sufficient tension so as to force the wheel 12 between the core slabs 2 to keep them separated. The wheel 12 is positioned to follow a short distance behind the saw 9.

The saw carriage means 8 is driven along the support rails 7 by a suitable motor 14 and drive means. The drive means shown comprises: a gear reducer 15 connected to the motor 14 by a belt 15a; a carriage chain sprocket 17 connected with the gear reducer 15 by a chain 16; and an endless chain 18 connecting the sprocket 17 with the saw carriage means 8.

A motor 19 is mounted on the saw carriage means 8 and connected with the saw 9 to rotate the latter.

The saw blade used is preferably a masonry type saw blade, having a diamond cutting edge.

A lubricant is preferably provided at the cutting edge of the saw during the cutting operation. A suitable lubricant, which does not significantly alter the sample of tar sand material, is water. To that end, lubricant water is added near the centre of the rotating saw 9. The water spreads to the cutting edge, where it is needed. If added directly to the cutting edge, the water is merely thrown off. A trough 20 located under the sawing area carries away waste water.

It is desirable to cut the core 1, encased in a plastic sheath, into short lengths before slabbing. This is easily done on the same machine A by placing the core 1 in holding brackets 21a placed at 90° to the direction of saw travel, as shown in FIG. 2. Such brackets 21a are disposed on support means 21. The bobbin 10 is raised on its spring-loaded arm 11, the core slab 2 placed in the brackets 21a, and the saw 9 is passed transversely through the core.

In operation, the core 1 is placed in the cradle means 3, the motor 14 is actuated to cause the chain 18 to move the saw carriage means 8 along the rails 7, thereby causing the saw 9 to cut transversely through the core 1 along its length and produce a pair of semi-circular slabs 2.

The Triangular Sample Machine

Figure 4:
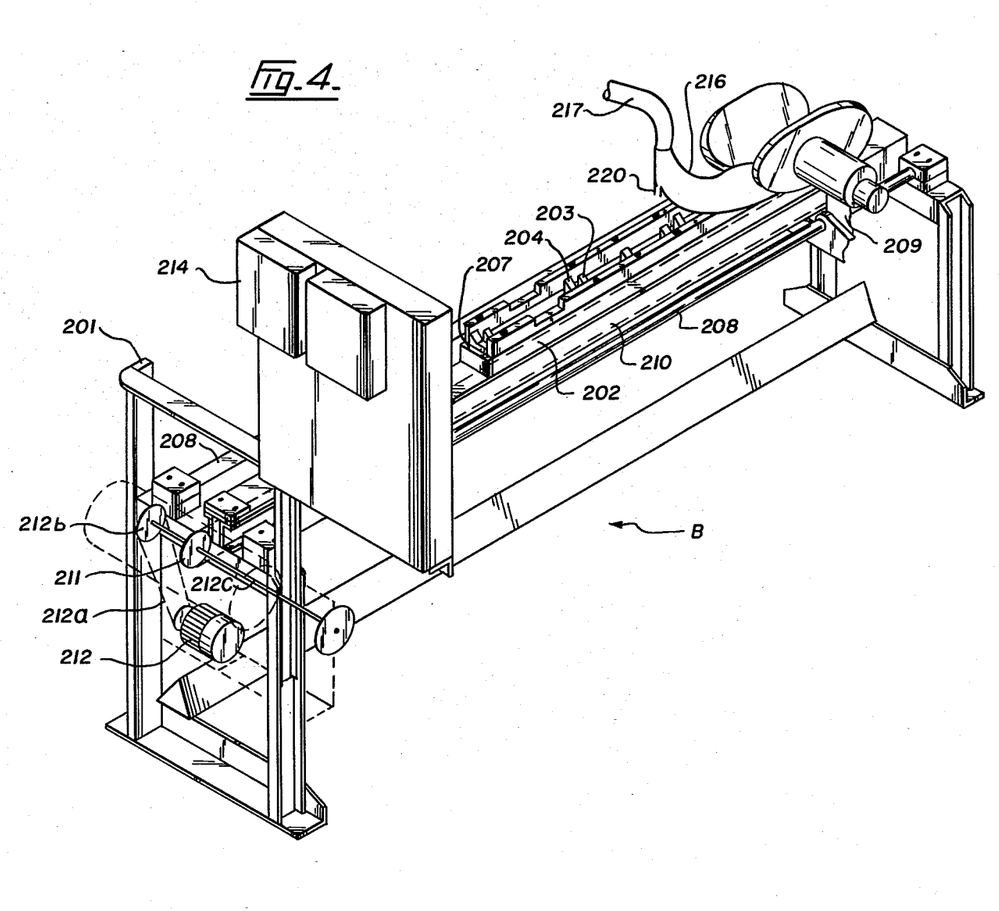
FIG. 4 is a perspective view of the triangular sample machine, with detail of the saws as set on the carriage.
Figure 5:
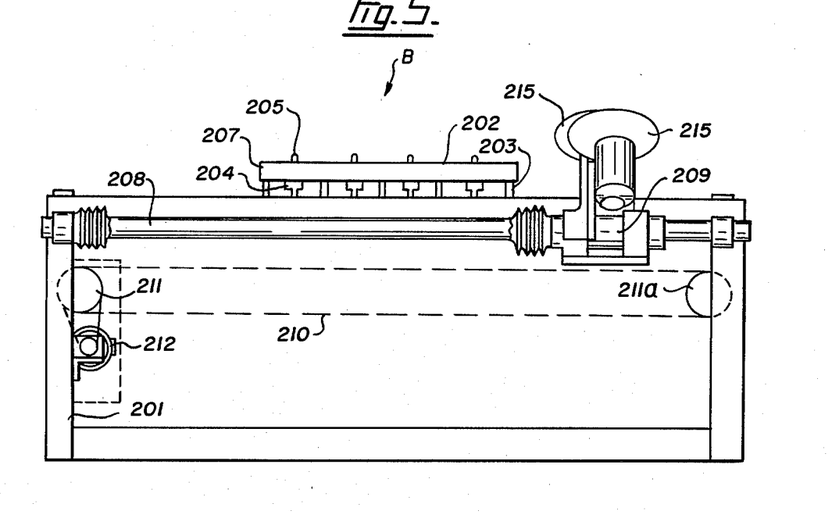
FIG. 5 is a side view of the triangular sample machine.
Figure 6:
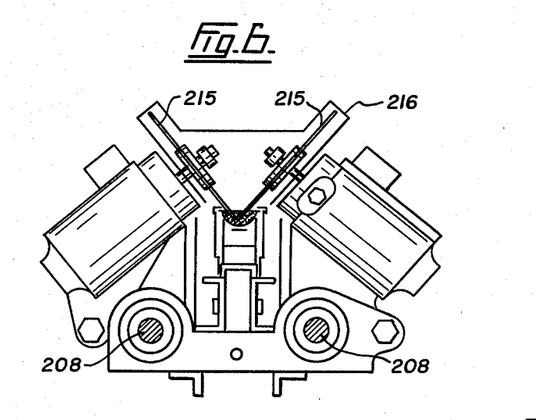
FIG. 6 is an end view of the triangular sample machine saws set on the saw carriage, showing the relationship of the carriage to the guide shafts, and the positioning of the core slab.

This machine B is illustrated in FIGS. 4, 5 and 6. It includes a frame 201 on which are mounted the other components.

Figure 4A:
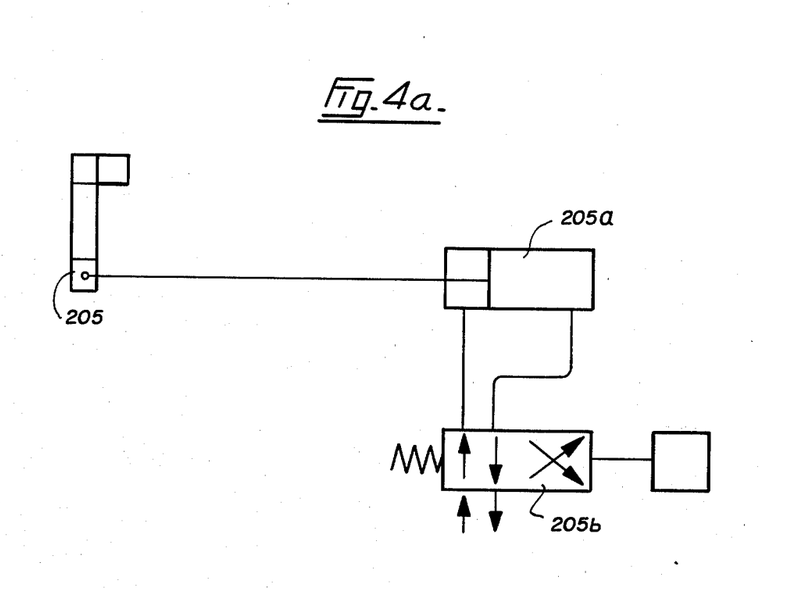
FIG. 4a is a schematic showing a slab-holding hinged stop and the means for actuating it.
Figure 4B:
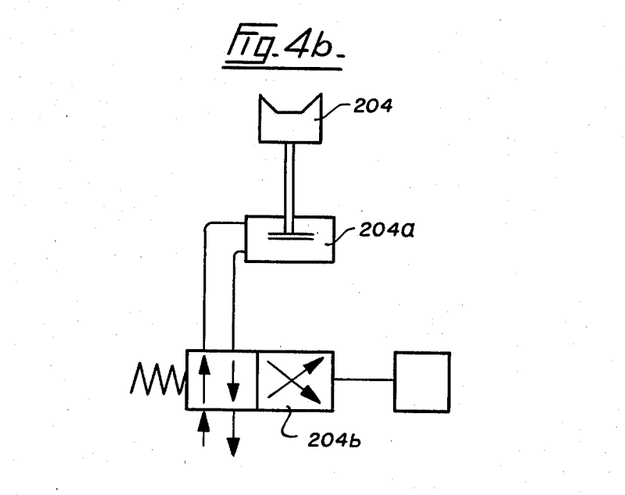
FIG. 4b is a schematic showing a cradle bracket and the means for actuating it.

More particularly, a horizontally extending cradle 202 is mounted on the frame 201. The cradle 202 comprises an array of fixed support brackets 203 and vertically movable brackets 204. As shown schematically in FIG. 4b, pneumatic cylinders 204a are provided for biasing the brackets 204 up or down. The cradle 202 further comprises a series of hinged stops 205 which may be rotated by cylinders 205a to engage and hold down the core slab 2. The cylinders 204a and 205a are suitably controlled through solenoid valve 204b and 205b respectively. The cradle 202 further comprises end stops 207 which limit axial displacement of the slab 2.

Thus, the cradle 202 is capable of lifting the core slab 2 to a pre-determined height and firmly holding it there, so that substantially the same volume of triangular sample may be cut from each slab.

Coring programs usually require the processing of large amounts of core, and it is therefore helpful for the sampling process to be largely mechanized. The movable brackets 204 and hinged stops 205 reduce the manual labour to be performed by the operators, and the time consumed in processing each slab 2.

Thus, to this point, there is provided frame means carrying cradle means for supporting and holding the core slab in position for cutting.

The frame 201 carries a pair of horizontal shafts 208. These shafts 208 extend parallel to the cradle 202 and the core slab 2 resting on it. The shafts 208 provide carriage support means for a purpose explained below.

A saw carriage 209 is mounted on the shafts 208 for movement therealong. An endless chain 210 is mounted on sprockets 211, 211a carried by the frame 201 and is connected with the carriage 209. The chain 210 functions to move the saw carriage 209 along the shafts 208. An electric motor 212 drives the chain 210 through a chain 212a, a sprocket 212b and shaft 212c on which the drive sprocket 211 is mounted. Thus there is provided saw carriage means mounted on the carriage support means for movement therealong.

Control means 214 are provided for controlling the starting, stopping, speed and direction of movement of the chain 210. Such means 214 are only shown schematically as they are conventional. Alternatively, of course, the saw carriage 209 may be freely movable along the shafts 208 and may be shifted by hand.

A pair of angularly disposed, driven, circular saws 215 are mounted on the saw carriage 209. The saws 215 are preferably positioned so that their lower margins are slightly spaced apart, as shown in FIG. 6. The blades of the saws preferably may be of the diamond-edge type used for masonry work.

Figure 8:
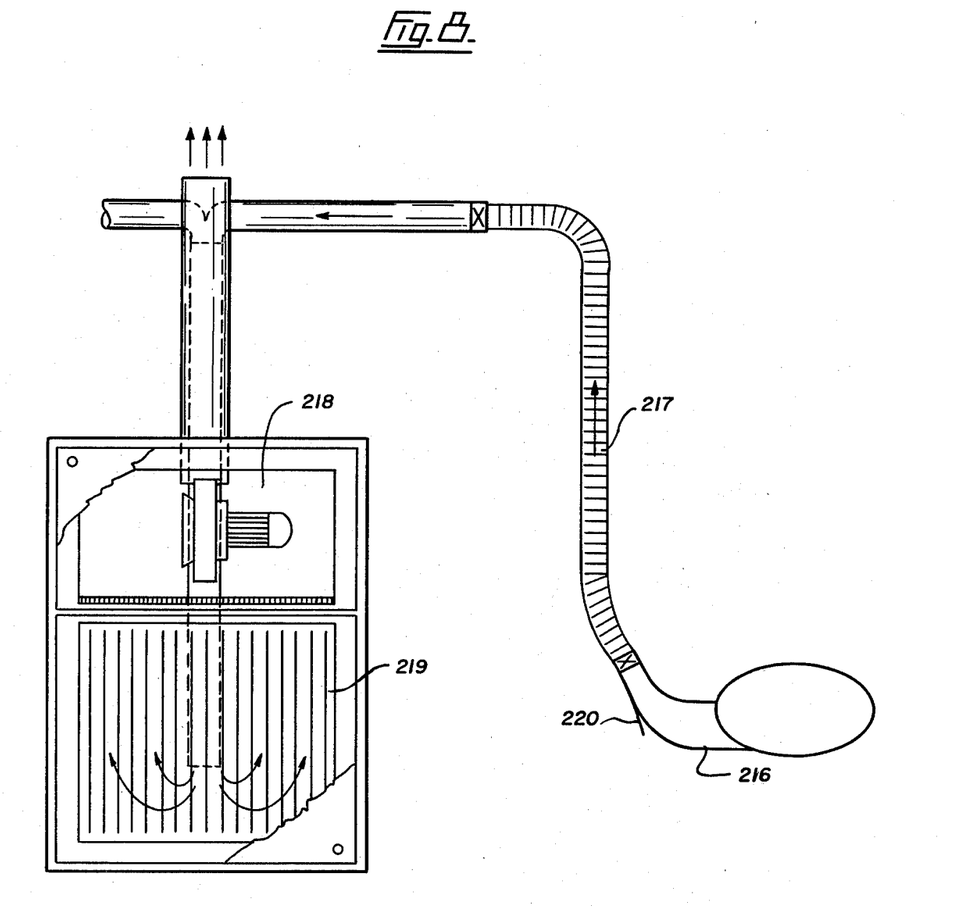
FIG. 8 is a front view of the dust-collection apparatus for use in conjunction with the triangular sample apparatus.

Means may be provided to draw off the dust generated by the action of the saws 215 cutting into the core slab 2. In the preferred embodiment shown in FIG. 8, a V-shaped suction nozzle 216 is attached to the advancing side of the saw carriage 209. The nozzle 216 is sized and positioned so that dust from each saw blade is thrown into the corresponding leg of the V. The outlet of the nozzle 216 is connected to a flexible conduct 217 which leads to an air fan 218 and discharges into dust filters 219. We employ equipment available from Torit Div., Donaldson Company, Inc., St. Paul, Minn., U.S.A. The motion imparted to the dust particles is enough to prevent build-up of dust in the pipework of the cleaning equipment, and keeps the sawing area clean. At the bend in the nozzle a small but fast-flowing stream of air is allowed to enter the piping at inlet 220, and this prevents build-up of dust at the bend. Dust is reduced if the blades rotate upwardly into the core slab.

In operation, with the saw carriage 209 in the start position, the core slab 2 is placed in the cradle 202. The rotatable stops 205 are turned, to overhang the edge of the cradle, and the movable brackets 204 are raised to lift the slab 2 such that the upper edges of the slab engage against the underside of the stops. The saws 215 are set in motion and the saw carriage 209 is pulled toward the opposite end of the machine by the chain 210. The saw blades pass through the core slab 2 lengthwise to saw a pair of angularly directed cuts 221 into the central portion of the slab, thereby forming a longitudinal sample portion 222 having a generally triangular cross-section of substantially constant cross-sectional area.

Figure 7:
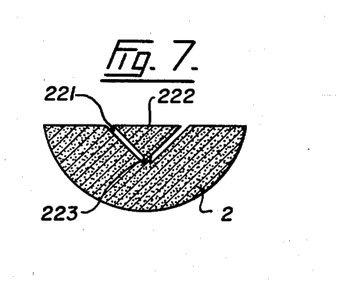
FIG. 7 is a cross-section of the slab of core after passage of the saws of the triangular sample machine therethrough, showing the bridging portion left to connect the apex of the sample to the remainder of the slab.

If the lower margins of the saw blades are slightly spaced apart, the apex 223 of the sample portion 222 remains integral with the main body of the core slab 2. The sample portion 222 can subsequently be broken away and lifted out using a spatula. This is desirable because, if the cuts are deep enough to sever the sample portion 222 from the slab, there is a tendency for the sample portion to break up and get jumbled, due to the saw vibration.

The Cryogenic Grinding Machine

Figure 9:
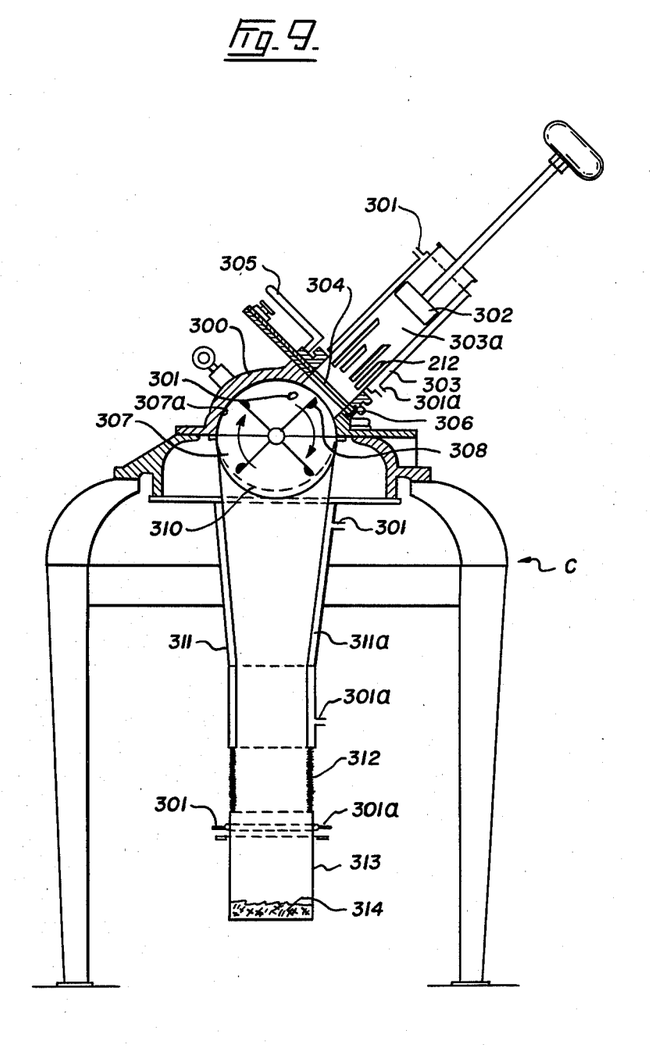
FIG. 9 is a sectional view of the cryogenic grinding machine showing sample feeding means, grinding means, and ground sample collecting means.

The grinder C is operative to grind the triangularly shaped sample portions 222 into a finely divided, generally homogeneous sample of the original tar sand core. This ground sample can then be subsampled to obtain smaller samples representative of the original core.

It is desirable to perform the grinding operation under cryogenic conditions. Without adequate cooling the bitumen adheres to the grinding equipment and loss of this bitumen renders the sample non-representative.

The grinder C used for this grinding process is shown in FIG. 9. It includes: feeding means for introducing the still-frozen longitudinal triangularly shaped sample portions 222 into the grinder; grinding means operative to pulverize the sample portions into a finely divided form; and receiving means to collect the pulverized sample for further sub-sampling.

Preferably the entire grinder C is cooled to cryogenic conditions. Liquid nitrogen is the preferred cooling medium for this purpose, since it provides rapid, intense cooling while having no chemical effect on the sample. Liquid nitrogen is passed into the grinder C at inlets 301 in the feeding, grinding and receiving means. Outlets 301a are also provided to allow nitrogen gas to circulate around the equipment. Nitrogen introduced into the grinding chamber 307a escapes through the porous cloth sleeve 312.

The feeding means preferably comprises a housing 300 having a cylindrical feed chamber 303 extending therefrom. A hand-operated piston 302 is positioned to reciprocate within the chamber 303. A plate 304 is movably interposed between the housing 300 and cylindrical chamber 303. The plate 304 is pivotally connected at 306 with the housing 300. An aperture extends through the plate 304. The plate 304 may be rotated by its handle 305 about the pivot connection 306 to bring the aperture into register with the bore 303a of the chamber 303 and thereby provide communication between said bore and a hammer mill 307 carried by the housing 300.

The grinding means is a conventional hammer mill 307 comprising a drum 307a with hammers 308 adapted to rotate therein. The lower wall of the drum 307a is a screen 310, through which the pulverized sample drops. Oversize material continues to circulate until ground to the desired size.

The receiving means comprises an insulated metal funnel 311, extending down from the screen 310 and equipped with nitrogen-circulating cavities 311a, a porous cloth sleeve 312 hanging from the funnel 311, and a receiver vessel 313 in which the ground sample 314 is collected. The porous sleeve 312 allows gaseous nitrogen to escape while the comminuted sample drops into the vessel 313.

In operation, the bore 303a of the chamber 303 is charged with triangularly shaped core samples 222. The gas tight piston 302 is then inserted into the bore 303a. Nitrogen is circulated to cool the machine and its contents. The plate 304 is then shifted to align the plate aperture with the bore 303a. The machine is then ready to permit the samples to be forced into the hammer mill 307. The motor (not shown) of the hammer mill is actuated to rotate the hammers 308 and the piston 302 pushed downwardly to force the samples 222 into the hammer mill 307, where they are pulverized, the product drops through the screen 310 into the receiver vessel 313.

EXAMPLES

The effectiveness of the cryogenic grinding machine in producing representative sub-samples was tested in laboratory experiments.

1. Tar sand was homogenized by hand to provide a comparison with results from cryogenic grinding. The tar sand was laid on a sheet of clear plastic and chopped to small size using a broad spatula. An analysis-sized sub-sample was withdrawn by reducing the size of the tar sand mass by consecutive coning and quartering. This involved arranging the homogenized tar sand in an even pile, dividing approximately into quarters with the spatula and retaining two opposite quarters and discarding the rest. Repetition of quartering on the residue of each step led to a representative sample. This was analysed for oil, water, and mineral solids by evaporation. Oil adhering to the spatula and plastic sheet was also collected by solvent washing, to ensure that all oil was accounted for. The results in Table I show the good agreement for the hand and cryogenic grinding over a wide range of tar sand oil levels.

TABLE I

| Hand Homogenized | By Cryogenic Grinder |
| --- | --- |
| 3.49% Oil | 3.50% Oil |
| 12.12 | 12.03 |
| 7.54 | 7.66 |
| 10.71 | 10.51 |
| 12.39 | 12.21 |
| 5.63 | 5.85 |
| 0.89 | 0.97 |

2. Lack of hold-up of sample in the apparatus was demonstrated by input/output ratio. Earlier versions showed severe loss as material was held up in or blown out of the device whereas in the best mode form losses are within an acceptable range for analytical purposes (Table II).

TABLE II

| Input | Output | Remarks on Features of the Device |
|---|---|---|
| g | g | |
| 434 | 250 | Cyclone blower used to re-cycle nitrogen |
| 367 | 282 | Long sleeve (cotton) at 312 (FIG. 9) |
| 485 | 439 | Nylon sleeve at 312 (FIG. 9) |
| 435 | 341 | "Dead" zones in funnel 311 due to walls being insufficiently vertical |
| 457 | 360 | Modified funnel 311 with more vertical walls |
| 511 | 488 | Input/Output improves as holes in sleeves 312 get plugged |
| 290 | 291 | |
| 353 | 343 | |
| 264 | 258 | Preferred embodiment |
| 416 | 410 | |
| 333 | 332 | |
| 378 | 379 | |
| 282 | 281 | |

3. Grinding should be sufficiently vigorous to homogenize the feed but not so intense as to comminute the sand particles themselves. At 2,000 rpm the hammer mill homogenization was adequate. No increase in fine matter was observed. Hence the combination of adequate homogenization without inordinate fines content is achieved with the invention.

PARTICLE SIZE DISTRIBUTION FOR TAR SAND SAMPLES BEFORE AND AFTER CRYOGENIC GRINDING*

PARTICLE SIZE DISTRUBUTION

| SAMPLE NO. | −325 mesh | | | −200 +325 mesh | | | −100 +200 mesh | | | +100 mesh | | |
|---|---|---|---|---|---|---|---|---|---|---|---|---|
| | Before Grinding | After Grinding | Diff. | Before Grinding | After Grinding | Diff. | Before Grinding | After Grinding | Diff. | Before Grinding | After Grinding | Diff. |
| #1 | 29.46 | 27.19 | −2.27 | 4.14 | 3.67 | −0.47 | 29.28 | 31.72 | +2.44 | 37.12 | 37.43 | +0.31 |
| #2 | 19.72 | 21.31 | +1.59 | 6.93 | 5.65 | −1.28 | 50.28 | 52.91 | +2.63 | 23.07 | 20.13 | −2.94 |
| #3 | 63.81 | 61.53 | −2.28 | 13.46 | 12.03 | −1.43 | 21.75 | 25.35 | +3.60 | 0.98 | 1.09 | −0.11 |
| | Mean Difference −0.99% | | | Mean Difference −1.06% | | | Mean Difference +2.89% | | | Mean Difference −0.84% | | |

*Mikropul Pulverizer Speed was 2,000 r.p.m.

The embodiments of the invention in which an exclusive property or privilege is claimed are defined as follows:

1. A method for sampling a frozen core of tar sand which comprises:
    cutting the core transversely to form a pair of slabs, each having a flat face and a curved face;
    sawing a pair of angularly directed cuts into the central portion of such a slab along at least part of its length to form a longitudinal sample portion having a generally triangular cross-section of substantially constant area;
    recovering the sample portion; and
    grinding at least part of the still frozen sample portion to form a generally homogeneous sample.

2. The method as set forth in claim 1 wherein:
    grinding is conducted under cryogenic conditions to maintain the material being ground frozen.

3. A sampling apparatus for cutting a longitudinal sample portion from a substantially semi-circular slab of frozen tar sand core comprising:
    frame means;
    cradle means carried by the frame means for supporting and holding the slab in position for cutting with its flat face fixed in a pre-determined plane;
    carriage support means carried by the frame means and extending substantially parallel to said plane along said slab;
    saw carriage means mounted on the support means for movement therealong;
    a pair of angularly disposed, driven circular saws carried by the carriage means and operative to make non-intersecting cuts into the central portion of the slab to form a longitudinal sample portion having a generally triangular cross-section of substantially constant area, said sample portion having an apex still attached to the main body of the slab;
    whereby a sample portion may be produced which can easily be broken away from the slab and recovered.

* * * * *